United States Patent [19]

Sirrenberg et al.

[11] 4,064,267
[45] Dec. 20, 1977

[54] 2',3,6'-TRICHLORO-4-CYANO-4'-[N-(N'-(O-SUBSTITUTED-BENZOYL))-UREIDO]-DIPHENYL ETHER INSECTICIDES

[75] Inventors: Wilhelm Sirrenberg, Sprockhoevel; Jürgen Schramm, Dormagen; Erich Klauke, Odenthal; Ingeborg Hammann, Cologne; Wihelm Stendel, Wuppertal, all of Germany

[73] Assignee: Bayer Aktiengesellschaft, Leverkusen, Germany

[21] Appl. No.: 704,708

[22] Filed: July 12, 1976

[30] Foreign Application Priority Data

July 16, 1975 Germany .............................. 2531743

[51] Int. Cl.$^2$ ....................... A01N 9/20; C07C 121/78
[52] U.S. Cl. .................. 424/304; 260/465 D; 260/465 E
[58] Field of Search .................... 260/465 D; 424/304

[56] References Cited

U.S. PATENT DOCUMENTS 3,992,553  11/1976  Sirrenberg et al. .................. 424/304

Primary Examiner—Dolph H. Torrence
Attorney, Agent, or Firm—Burgess, Dinklage & Sprung

[57] ABSTRACT

2',3,6'-Trichloro-4-cyano-4'-[N-(N'-o-substituted-benzoyl))-ureido]-diphenyl ethers of the formula

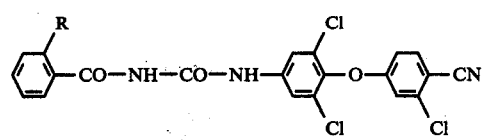

in which
R represents chlorine, fluorine, bromine or methyl, which possess insecticidal properties.

8 Claims, No Drawings

2',3,6'-TRICHLORO-4-CYANO-4'-[N-(N'-(O-SUBSTITUTED-BENZOYL))-UREIDO]-DIPHENYL ETHER INSECTICIDES

The present invention relates to and has for its objects the provision of particular new 2',3,6'-trichloro-4-cyano-4'-[N-(N'-(o-substituted-benzoyl))-ureido]-diphenyl ethers, i.e. benzoylureido-diphenyl ethers of the class described wherein the substitution is chloro, fluoro, bromo or methyl, which possess insecticidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from German Published Specification DOS 2,123,236 that certain benzoylureas, such as, for example, N-(2,6-dichlorobenzoyl)-N'-(4-chlorophenyl (Compound A) and -3,4-dichlorophenyl)-urea (Compound B), possess insecticidal properties. However, their activity is not always satisfactory if low concentrations are used.

The present invention provides as new compounds the benzoylureido-diphenyl ethers of the general formula

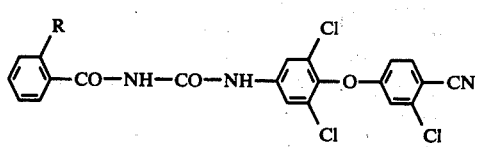

in which

R represents chlorine, fluorine, bromine or methyl.

Surprisingly, the benzoylureido-diphenyl ethers according to the invention have a substantially better insecticidal action than the nearest compounds of analogous structure and of the same type of action previously known from the state of the art. The compounds according to the invention thus represent a genuine enrichment of the art.

The present invention provides a process for preparation of a benzoylureido-diphenyl ether of the formula (I) in which a. the phenoxyaniline of the formula

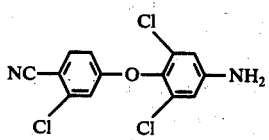

is reacted with a benzoylisocyanate of the general formula

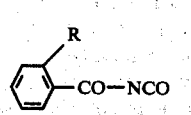

in which

R has the above-mentioned meaning, if appropriate in the presence of a solvent, or b. the 4-isocyanato-diphenyl ether of the formula

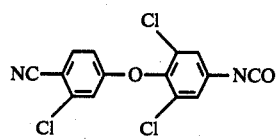

is reacted with a benzamide of the general formula

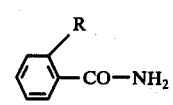

in which

R has the above-mentioned meaning, if appropriate in the presence of a solvent.

If, following process variant (a), 4-(3'-chloro-4'-cyanophenoxy)-3,5-dichloro-aniline and 2-chlorobenzoylisocyanate are used as starting materials, and, following process variant (b), 4-(3'-chloro-4'-cyanophenoxy)-3,5-dichloro-phenylisocyanate and 2-fluorobenzamide are used as starting materials, the courses of the reactions can be represented by the following formula schemes:

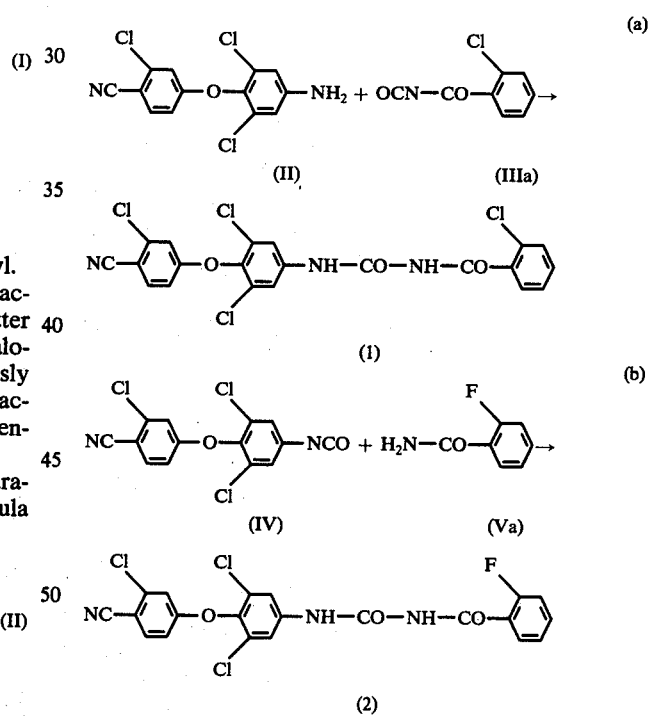

2-Chlorobenzoylisocyanate, to be used as a starting material, is known from the literature and can, like the other benzoylisocyanates, be prepared in accordance with generally customary processes [see A. J. Speziale et al., J. Org. Chem. 30(12), pages 4306–4307 (1965)].

2-Fluorobenzamide and the other benzamides are known and can be prepared in accordance with generally customary processes (see Beilsteins Handbuch der organischen Chemie (Beilstein's Handbook of Organic Chemistry), Volume 9, page 336). The phenoxyaniline (II) can be prepared in accordance with generally customary processes, for example from an alkali metal aminophenolate and 1,3-dichloro-4-cyanobenzene in a solvent, for example dimethylsulphoxide (see also J. Schramm et al., Justus Liebigs Annalen der Chemie 1970, 740, 169–179). The amino group can be converted to the isocyanate group in accordance with generally customary processes, for example by reaction with phosgene, whereby the 4-isocyanatodiphenyl ether of the formula (IV) is obtained.

The following may be mentioned as individual benzoylisocyanates (III) and benzamides (V) to be reacted in accordance with the process: 2-chloro-, 2-fluoro-, 2-bromo- and 2-methyl-benzoylisocyanate, and 2-chloro-, 2-fluoro-, 2-bromo- and 2-methyl-benzamide.

The process variants for the preparation of the compounds according to the invention are preferably carried out in the presence of suitable solvents or diluents. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride, chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and benzonitrile.

The reaction temperature can be varied within a fairly wide range. In general, the reaction is carried out at between 0° and 120° C, preferably at from 60° to 85° C.

In general, the reaction is allowed to take place under normal pressure.

To carry out the process, the reactants are preferably employed in equimolar amounts. An excess of one or other component produces not significant advantages.

The 4-isocyanato-diphenyl ether (IV) to be employed in process variant (b) can be used as such or, without intermediate isolation, in the form of its reaction mixture as obtained from the reaction of amine with phosgene. To this reaction mixture, in one of the above-mentioned solvents, is added the benzamide, for example fluorobenzamide. The reaction is carried out under the desired conditions and the product which separates out is isolated in the customary manner by filtration, washing and, if appropriate, recrystallization.

The compounds are obtained in a crystalline form having a sharp melting point.

As already mentioned, the benzoylureido-diphenyl ethers according to the invention are distinguished by an excellent insecticidal activity, which is accompanied by advantageous levels of toxicity to warm-blooded animals and a good toleration by plants.

For this reason, the compounds according to the invention can be employed successfully as pesticides in plant protection against biting and sucking insects. They may be furthermore used in the veterinary medicine field.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (*Coccina*), for example the oleander scale (*Aspidiotus hederae*) and the soft scale (*Lecanium hesperidum*) as well as the grape mealybug (*Pseudococcus maritimus*), thrips (*Thysanoptera*), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as Euscelis bilobatus and *Nepthotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (*Galleria mellonella*).

Also to be classed with the biting insects are beetles (*Coleoptera*), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry bettle (*Byturus tomentosus*), the bean weevil (*Bruchidius = Acanthoscelides obtectus*), the leather beetle (*Dermestes frischi*), the khapra beetle (*Trogo-derma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (Oryzae-*philus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such an ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aëdes aegypti*), the northern house mosquito (*Culex pipens*) and the malaria mosquito (*Anopheles stephensi*).

With the mites (*Acarina*) there are classed, in particular, the spider mites (*Tetranychidae*) such as the two-spotted spider mite (*Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks such as the relapsing fever tick (*Ornithodorous moubata*).

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plane compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispercible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylene, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall all compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liter/hectare are needed, and often amounts only up to about 15 to b 1000 g/hectare, preferably b 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. insects, which comprises applying to at least one of correspondingly (*a*) such insects, and (*b*) the corresponding habitat thereof, i.e. the locus to be protected, e.g. to a growing crop, to an area where a crop is to be grown or to a domestic animal, a correspondingly combative or toxic amount, i.e. insecticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, or course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Test with parasitic fly larvae

Solvent: 35 parts by weight of ethylene polyglycol monomethyl ether 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all of the larvae has been killed and 0% means that no larvae had been killed.

The active compounds investigated, the concentrations of the active compounds used and the results obtained can be seen from the table which follows:

EXAMPLE 2

Plutella test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica cleracea*) were sprayed with the preparation of the active compound until dew moist and were then infected with caterpillars of the diamond-back moth (*Plutella maculipennis*).

After the specified periods of time, the degree of destruction was determined as a precentage: 100% means that all of the caterpillars were killed whereas 0% means that none of the caterpillars were killed.

Table 1

(Test on *Lucilia cuprinia*, resistant)

| Active compound | Active compound concentration in ppm | Degree of destruction in % after 1 day |
|---|---|---|
| Cl-C₆H₃(Cl)-CONH-CONH-C₆H₄-Cl (known) (A) | 1000 | 0 |
| F-C₆H₄-CONH-CONH-C₆H₂(Cl)₂-O-C₆H₃(Cl)-CN (2) | 1000<br>300 | 100<br>100 |
| CH₃-C₆H₄-CONH-CONH-C₆H₂(Cl)₂-O-C₆H₃(Cl)-CN (3) | 1000<br>300 | 100<br>100 |
| Cl-C₆H₄-CONH-CONH-C₆H₂(Cl)₂-O-C₆H₃(Cl)-CN | 1000<br>300 | 100<br>100 |

The active compounds, the concentrations of the active compounds, the evaluation times and the results can be seen from the following table:

Table 2

(*Plutella* test)

| Active compounds | Active compound concentration in % | Degree of destruction in % after 8 days |
|---|---|---|
| Cl-C₆H₃(Cl)-CO-NH-CO-NH-C₆H₄-Cl (known) (A) | 0.1<br>0.01 | 65<br>0 |

Table 2-continued
(*Plutella* test)

| Active compounds | Active compound concentration in % | Degree of destruction in % after 8 days |
|---|---|---|
| 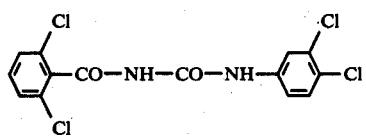 (known) (B) | 0.1<br>0.01<br>0.001 | 100<br>100<br>15 |
| 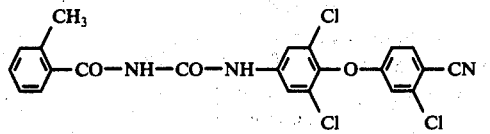 (3) | 0.1<br>0.01<br>0.001 | 100<br>100<br>100 |
| 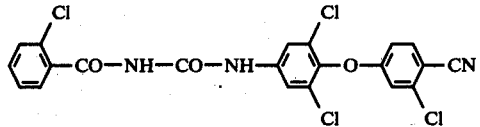 (1) | 0.1<br>0.01<br>0.001 | 100<br>100<br>100 |
| 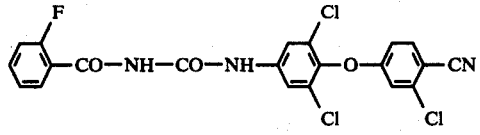 (2) | 0.1<br>0.01<br>0.001 | 100<br>100<br>100 |
| 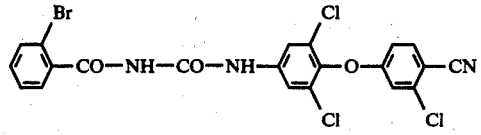 (4) | 0.1<br>0.01<br>0.001 | 100<br>100<br>100 |

EXAMPLE 3

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all of the beetle larvae had been killed whereas 0% means that none of beetle larvae have been killed.

The active compounds, the concentrations of the active compounds, the evaluation times and the results can be seen from the following table:

Table 3
(*Phaedon* larvae test)

| Active compounds | Active compound concentration in % | Degree of destruction in % after 3 days |
|---|---|---|
| 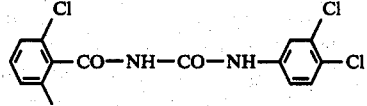 (known) (B) | 0.1<br>0.01 | 100<br>15 |

Table 3-continued (*Phaedon* larvae test)

| Active compounds | Active compound concentration in % | Degree of destruction in % after 3 days |
|---|---|---|
| 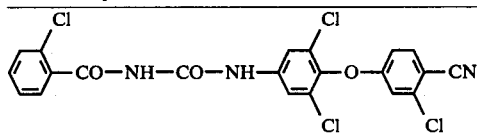 (1) | 0.1<br>0.01 | 100<br>90 |

The process of the present invention is illustrated by the following preparative Examples.

EXAMPLE 4

(1)

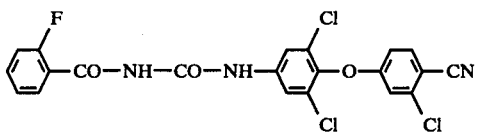

A solution of 5.5 g (0.03 mole) of b 2-chlorobenzoylisocyanate in 20 ml of toluene was added dropwise at 80° C to 9.4 g (0.3 mole) of 4-(3'-chloro-4'-cyanophenoxy)-3,5-dichloroaniline in 100 ml of toluene. The batch was stirred for 1 hour at 60° C. After cooling, the product which had precipitated was filtered off and washed first with toluene and then with petroleum ether. After drying, 10.0 g (67% of theory) of analytically pure 2',3,6'-trichloro-4-cyano-4'-[N-(N'-(o-chlorobenzoyl))-ureido]-diphenyl ether of melting point 194° C were obtained.

EXAMPLE 5

(2)

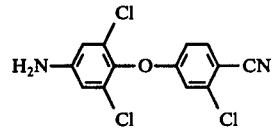

A solution of 3.3 g )0.02 mole) of 2-fluorobenzoylisocyanate in 20 ml of toluene was added dropwise at 80° C to a solution of 6.3 g (0.02 mole) of 4-(3'-chloro-4'-cyanophenoxy)-3,5-dichloroaniline in 100 ml of toluene. The batch was stirred for 1 hour at 80° C. The substance which separated out was filtered off after cooling the reaction mixture to 20° C, and was washed with toluene and petroleum ether. After drying, 7 g (73% of theory) of 2',3,6'-trichloro-4-cyano-4'-[N-(N'-(2-fluorobenzoyl))-ureido]-diphenyl ether of melting point 201° C were obtained.

The following compounds were obtained by methods analogous to those described in Examples 4 and 5.

| Compound No. | Formula | Physical data (melting point, °C) | Yield (% of theory) |
|---|---|---|---|
| 3 | 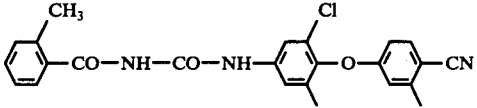 | 186 | 63 |
| 4 | 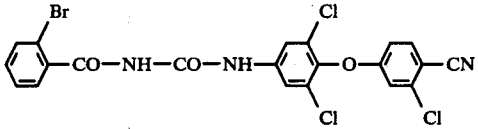 | 224 | 74 |

EXAMPLE 6

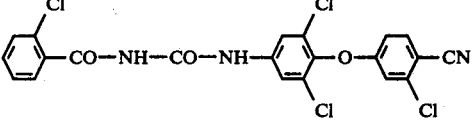

A solution of 32.5 g potassium hydroxide in 30 ml water was added to a mixture of 89 g (0.5 mole) 4-amino-2,6-dichlorophenol and 500 ml dimethylsulfoxide and under reduced pressure 200 ml liquid were distilled off. After that a solution of 91.5 g (0.5 mole) 2-chloro-4-nitro-benzonitrile in 150 ml dimethylsulfoxide was added dropwise to the residue. The batch was stirred for 2 hours at 80° C. The reaction mixture was poured into a solution of methanol/water and ice and the precipitating product was filtered off. The product was washed first with water and then recristallized from ethanol. 66 g (42% of the theory) 4-(3'-chloro-4'-cyanophenoxy)-3,5-dichloroanilide of melting point 130°-131° C were obtained.

It will be appreciated that the instant specification and examples are set forth by ways of illustration and not limitation, and that various modifications and changes may be made without departing from the spirit and scope of the present invention.

What is claimed is:

1. A 2',3,6'-trichloro-4-cyano-4'-[N-(N'-(o-substituted-benzoyl))-ureido]-diphenyl ether of the formula

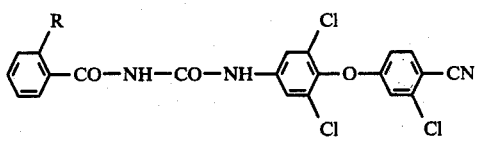

in which
R is chlorine, fluorine, bromine or methyl.

2. A benzoylureido-diphenyl ether according to claim 1 wherein such compound is 2′,3,6′-trichloro-4-cyano-4′-[N-(N′-(o-chlorobenzoyl))-ureido]-diphenyl ether of the formula

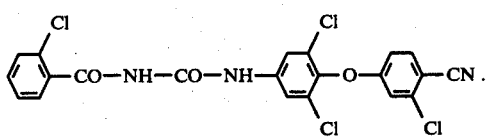

3. A benzoylureido-diphenyl ether according to claim 1 wherein such compound is 2′,3,6′-trichloro-4-cyano-4′-[N-(N′-(o-fluorobenzoyl))-ureido]-diphenyl ether of the formula

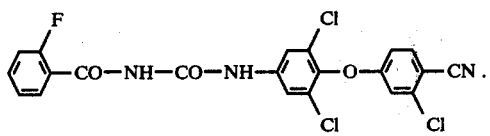

4. A benzoylureido-diphenyl ether according to claim 1 wherein such compound is 2′,3,6′-trichloro-4-cyano-4′-[N-(N′-(o-methylbenzoyl))-ureido]-diphenyl ether of the formula

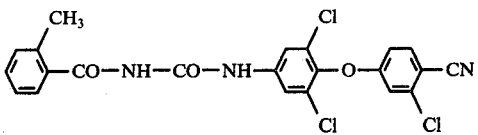

5. A benzoylureido-diphenyl ether according to claim 1 wherein such compound is 2′,3,6′-trichloro-4-cyano-4′-[N-(N′-(o-bromobenzoyl))-ureido]-diphenyl ether of the formula

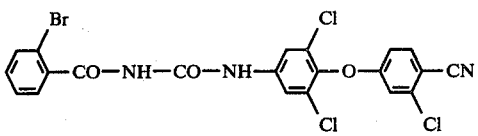

6. An insecticidal composition containing as active ingredient an insecticidally effective amount of a compound according to claim 1 in admixture with a diluent.

7. A method of combating insects which comprises applying to the insects or an insect habitat an insecticidally effective amount of a compound according to claim 1.

8. The method according to claim 7 in which said compound is
2′,3,6′-trichloro-4-cyano-4′-[N-(N-(o-chlorobenzoyl))-ureido]-diphenyl ether,
2′,3,6′-trichloro-4-cyano-4-cyano-4′-[N-(N′-(o-fluorobenzoyl))-ureido]-diphenyl ether,
2′,3,6′-trichloro-4-cyano-4′-[N-(N′-(o-methylbenzoyl))-ureido]-diphenyl ether, or
2′,3,6′-trichloro-4-cyano-4′-[N-(N′-(o-bromobenzoyl))-ureido]-diphenyl ether.

* * * * *

UNITED STATES PATENT AND TRADEMARK OFFICE
CERTIFICATE OF CORRECTION

PATENT NO. : 4,064,267
DATED : December 20, 1977
INVENTOR(S) : Wilhelm Sirrenberg et al It is certified that error appears in the above-identified patent and that said Letters Patent are hereby corrected as shown below:

Col. 4, line 66 - correct spelling of "Ornithodorus"
Col. 5, line 7 - change "plane" to -- plant --.
Col. 6, line 32 - change "liter" to -- liters --.
Col. 6, line 33 - cancel "b".
Col. 6, line 34 - cancel "b".
Col. 8, line 12- cancel "cleracea" and substitute --oleracea--.
Col. 11, line 44- cancel "0.3" and substitute -- 0.03 --.
Col. 11,line 62 - cancel ")" before "0" and substitute -- ( --.
Col. 12, line 57- correct spelling of "recrystallized".
Col. 14, line 30 cancel "-4-cyano " second occurrence Signed and Sealed this Twentieth Day of June 1978

[SEAL]

Attest:

RUTH C. MASON
Attesting Officer

DONALD W. BANNER
Commissioner of Patents and Trademarks